United States Patent
Huculak et al.

(10) Patent No.: US 8,109,937 B2
(45) Date of Patent: Feb. 7, 2012

(54) SURGICAL SYSTEM FOR INDICATION OF MEDIA TYPES

(75) Inventors: John C. Huculak, Mission Viejo, CA (US); David C. Buboltz, Upland, CA (US); Paul Hallen, Colleyville, TX (US)

(73) Assignee: Alcon Research, Ltd., Fort Worth, TX (US)

( * ) Notice: Subject to any disclaimer, the term of this patent is extended or adjusted under 35 U.S.C. 154(b) by 917 days.

(21) Appl. No.: 12/033,132

(22) Filed: Feb. 19, 2008

(65) Prior Publication Data

US 2008/0208207 A1    Aug. 28, 2008

Related U.S. Application Data

(60) Provisional application No. 60/891,263, filed on Feb. 23, 2007.

(51) Int. Cl.
*A61F 9/00* (2006.01)
(52) U.S. Cl. .................. 606/107; 604/30; 600/561
(58) Field of Classification Search ............... 606/107; 604/22, 30
See application file for complete search history.

(56) References Cited

U.S. PATENT DOCUMENTS

| | | | |
|---|---|---|---|
| 3,964,487 A | 6/1976 | Judson | |
| 4,024,866 A | 5/1977 | Wallach | |
| 4,126,137 A | 11/1978 | Archibald | |
| 4,223,676 A | 9/1980 | Wuchinich et al. | |
| 5,160,317 A | 11/1992 | Costin | |
| 5,249,121 A * | 9/1993 | Baum et al. | 606/1 |
| 5,279,547 A | 1/1994 | Costin | |
| 5,520,633 A | 5/1996 | Costin | |
| 5,669,876 A | 9/1997 | Schechter et al. | |
| 5,733,256 A | 3/1998 | Costin | |
| 6,290,690 B1 * | 9/2001 | Huculak et al. | 604/521 |
| 6,599,277 B2 | 7/2003 | Neubert | |
| 7,001,018 B1 | 2/2006 | Martin | |
| 7,837,660 B2 | 11/2010 | Jones et al. | |
| 2009/0158812 A1 | 6/2009 | Jones | |
| 2010/0156646 A1 | 6/2010 | Cull et al. | |

FOREIGN PATENT DOCUMENTS

| | | |
|---|---|---|
| EP | 0 424 687 A1 | 5/1991 |
| WO | WO02/26016 * | 9/2001 |
| WO | WO 02/26016 A2 | 4/2002 |
| WO | WO 03/047653 A1 | 6/2003 |
| WO | WO 2009/120184 A2 | 10/2009 |
| WO | WO 2009/120184 A3 | 10/2009 |

OTHER PUBLICATIONS

International Searching Authority, Written Opinion of the International Searching Authority, International Application No. PCT/2008/054377, Sep. 30, 2009, 7 pages.

* cited by examiner

*Primary Examiner* — Max Hindenburg
*Assistant Examiner* — Renee Danega

(57) ABSTRACT

A surgical system includes a surgical instrument, an aspiration flow rate measurement device, a vacuum force measurement device, and an indicator. The surgical instrument has an aspiration portion and is located in a media type. The aspiration flow rate measurement device is configured to measure the flow rate generated by the aspiration portion. The vacuum force measurement device is configured to measure the vacuum force generated by the aspiration portion. The indicator provides an indication of the media type in which the surgical instrument is located. The indication is based on aspiration flow rate measurement information, vacuum force measurement information, and an operation and configuration of the surgical instrument.

21 Claims, 4 Drawing Sheets

SURGICAL SYSTEM FOR INDICATION OF MEDIA TYPES

RELATED APPLICATIONS

This application claims priority to U.S. Provisional Patent Application No. 60/891,263 filed Feb. 23, 2007.

BACKGROUND OF THE INVENTION

The present invention relates to a surgical system for providing an indication of media types and more particularly to a system for indicating the type of media in which a surgical instrument is disposed.

Anatomically, the eye is divided into two distinct parts— the anterior segment and the posterior segment. The anterior segment includes the lens and extends from the outermost layer of the cornea (the corneal endothelium) to the posterior of the lens capsule. The posterior segment includes the portion of the eye behind the lens capsule. The posterior segment extends from the anterior hyaloid face to the retina, with which the posterior hyaloid face of the vitreous body is in direct contact. The posterior segment is much larger than the anterior segment.

The posterior segment includes the vitreous body—a clear, colorless, gel-like substance. It makes up approximately two-thirds of the eye's volume, giving it form and shape before birth. It is composed of 1% collagen and sodium hyaluronate and 99% water. The anterior boundary of the vitreous body is the anterior hyaloid face, which touches the posterior capsule of the lens, while the posterior hyaloid face forms its posterior boundary, and is in contact with the retina. The vitreous body is not free-flowing like the aqueous humor and has normal anatomic attachment sites. One of these sites is the vitreous base, which is a 3-4 mm wide band that overlies the ora serrata. The optic nerve head, macula lutea, and vascular arcade are also sites of attachment. The vitreous body's major functions are to hold the retina in place, maintain the integrity and shape of the globe, absorb shock due to movement, and to give support for the lens posteriorly. In contrast to aqueous humor, the vitreous body is not continuously replaced. The vitreous body becomes more fluid with age in a process known as syneresis. Syneresis results in shrinkage of the vitreous body, which can exert pressure or traction on its normal attachment sites. If enough traction is applied, the vitreous body may pull itself from its retinal attachment and create a retinal tear or hole.

Various surgical procedures, called vitreo-retinal procedures, are commonly performed in the posterior segment of the eye. Vitreo-retinal procedures are appropriate to treat many serious conditions of the posterior segment. Vitreo-retinal procedures treat conditions such as age-related macular degeneration (AMD), diabetic retinopathy and diabetic vitreous hemorrhage, macular hole, retinal detachment, epiretinal membrane, CMV retinitis, and many other ophthalmic conditions.

A vitrectomy is a common part of a vitreo-retinal procedure. A vitrectomy, or surgical removal of the vitreous body, may be performed to clear blood and debris from the eye, to remove scar tissue, or to alleviate traction on the retina. Blood, inflammatory cells, debris, and scar tissue obscure light as it passes through the eye to the retina, resulting in blurred vision. The vitreous body is also removed if it is pulling or tugging the retina from its normal position. Some of the most common eye conditions that require a vitrectomy include complications from diabetic retinopathy such as retinal detachment or bleeding, macular hole, retinal detachment, pre-retinal membrane fibrosis, bleeding inside the eye (vitreous hemorrhage), injury or infection, and certain problems related to previous eye surgery.

A surgeon performs a vitrectomy with a microscope and special lenses designed to provide a clear image of the posterior segment. Several tiny incisions just a few millimeters in length are made on the sclera at the pars plana. The surgeon inserts microsurgical instruments through the incisions such as a fiber optic light source to illuminate inside the eye, an infusion line to maintain the eye's shape during surgery, and instruments to cut and remove the vitreous body.

The surgical machines used to perform procedures on the posterior segment of the eye are very complex. Typically, such ophthalmic surgical machines include a main console to which numerous different tools are attached. The main console provides power to and controls the operation of the attached tools. The attached tools typically include probes, scissors, forceps, illuminators, vitrectors, and infusion lines. A computer in the main surgical console monitors and controls the operation of these tools.

In a vitrectomy, for example, the vitrector cuts the vitreous body which is then removed through aspiration. An infusion line supplies intraocular irrigating solution to assist in the removal of the cut vitreous tissue. To remove vitreous effectively, a surgeon keeps the vitrector in the vitreous at the interface between the intraocular irrigating solution and the vitreous itself. If the vitrector is not kept in the vitreous, it does not effectively remove the vitreous. This can prolong surgery resulting in inefficiencies and possible detrimental effects to the patient. It would be desirable to know if a surgical instrument, such as a vitrector, is properly placed in the eye.

SUMMARY OF THE INVENTION

In one embodiment consistent with the principles of the present invention, the present invention is a surgical system with a surgical instrument, an aspiration flow rate measurement device, a vacuum force measurement device, and an indicator. The surgical instrument has an aspiration portion and is located in a media type. The aspiration flow rate measurement device is configured to measure the flow rate generated by the aspiration portion. The vacuum force measurement device is configured to measure the vacuum force generated by the aspiration portion. The indicator provides an indication of the media type in which the surgical instrument is located. The indication of the media type in which the surgical instrument is located is based on aspiration flow rate measurement information, vacuum force measurement information, and an operation and configuration of the surgical instrument.

In another embodiment consistent with the principles of the present invention, the present invention is a method for identifying a media type in which a surgical instrument is located. The method includes receiving vacuum force information, receiving aspiration flow rate information, using the vacuum force information and the aspiration flow rate information to determine the media type in which the instrument is located, and providing an indication of the media type.

It is to be understood that both the foregoing general description and the following detailed description are exemplary and explanatory only and are intended to provide further explanation of the invention as claimed. The following description, as well as the practice of the invention, set forth and suggest additional advantages and purposes of the invention.

BRIEF DESCRIPTION OF THE DRAWINGS

The accompanying drawings, which are incorporated in and constitute a part of this specification, illustrate several embodiments of the invention and together with the description, serve to explain the principles of the invention.

DETAILED DESCRIPTION OF THE PREFERRED EMBODIMENTS

Reference is now made in detail to the exemplary embodiments of the invention, examples of which are illustrated in the accompanying drawings. Wherever possible, the same reference numbers are used throughout the drawings to refer to the same or like parts.

As noted above, during ophthalmic surgery, different media are removed from the eye. In this patent, media refers to the different substances that can be placed in the eye, such as irrigating solution (typically, a sterile saline solution), perfluorocarbon liquids, and silicone oil as well as the different substances and structures found in the eye, such as the vitreous. Typically, an infusion line provides sterile saline solution, an aspiration line removes media from the eye, and a surgical instrument operates on the eye. While the exemplary embodiments described herein are particular to ophthalmic surgery, the invention may also be used in any surgery in which media is removed from the body.

Different media in the eye have different properties that can be detected by the media's resistance to aspiration. The aspiration vacuum force required to remove the vitreous body after it is cut by a vitrector is different than the aspiration required to remove saline solution, perfluorocarbon liquid, or silicone oil. This resistance to aspiration can be used to determine the type of media itself for a given infusion flow rate, instrument configuration and instrument operation.

For any configuration and operation of a surgical instrument, a media's impedance can be characterized by its resistance to aspiration flow. At a given aspiration vacuum force and infusion flow rate, various media may be characterized by the vacuum force required to achieve an aspiration flow rate. In other words, a media's impedance (akin to its viscosity) will require a certain aspiration vacuum force to achieve an aspiration flow rate. The media may be identified based on the vacuum force and flow rate In a vitrectomy, the media types include: vitreous, perfluorocarbon liquid (a liquid with a high specific gravity that functions as a mechanical tool during vitreoretinal surgery, providing hydrokinetic manipulation of the detached retina. This high specific gravity allows the liquid to be infused over the posterior portion of the retina to facilitate retinal flattening and anterior displacement of sub-retinal fluid), silicone oil (a postoperative retinal tamponade used in vitreoretinal surgery), and sterile intraocular irrigating solution (such as BSS Plus by Alcon Laboratories, Inc. of Fort Worth, Tex.).

Figure 1:
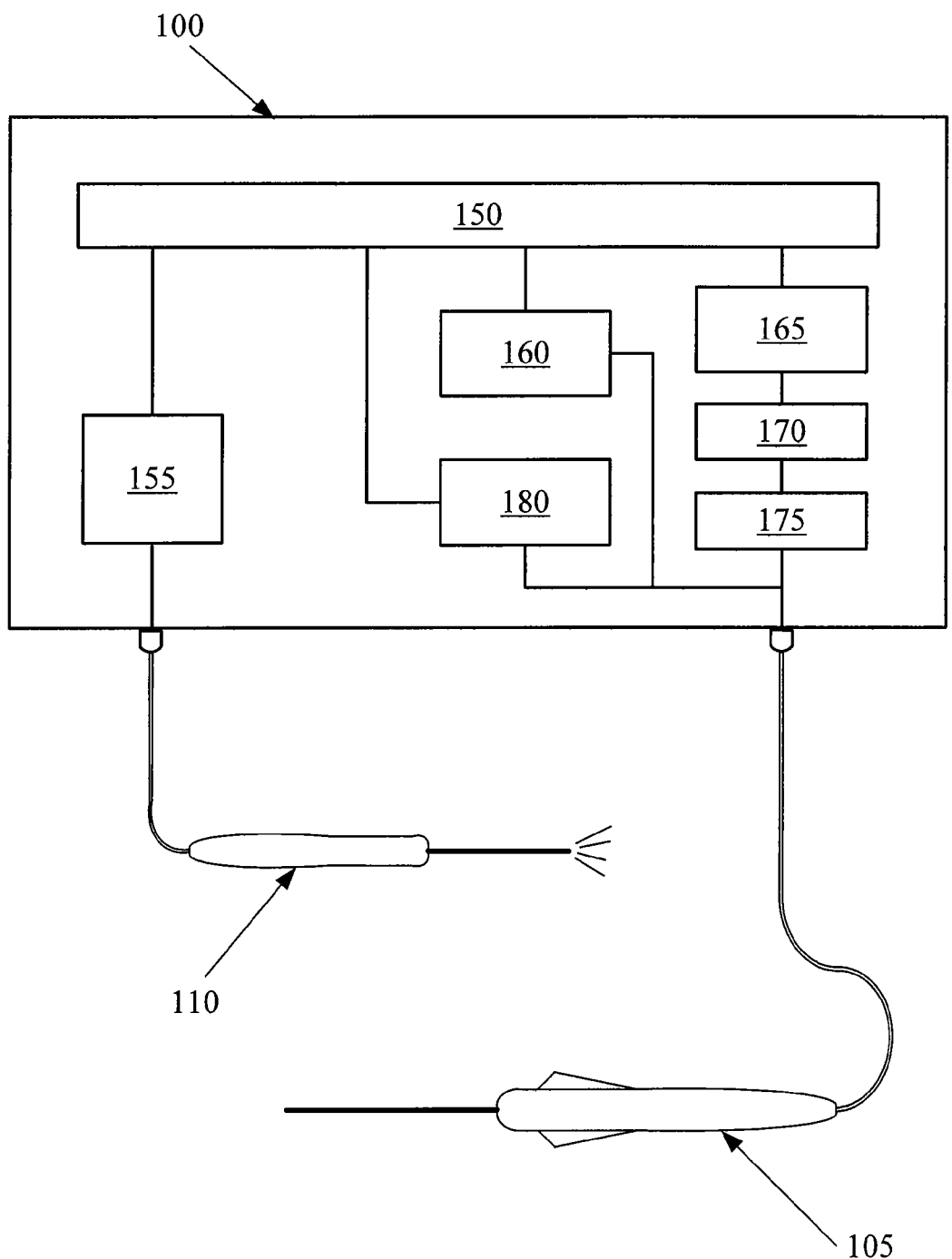
FIG. 1 is a block diagram of an ophthalmic surgical system for identifying media types according to an embodiment of the present invention.

FIG. 1 is a block diagram of an ophthalmic surgical system for identifying media types according to an embodiment of the present invention. In FIG. 1, a vitrector 105 and intraocular light 110 are each attached via a cable and connector to a surgical console 100. The surgical console includes a controller 150, a driver 155, an infusion pump 160, a vacuum generator 165, a vacuum force measurement device 170, a flow rate measurement device 175, and a vitrector driver 180. The controller interfaces with the driver 155, the infusion pump 160, the vacuum generator 165, the vacuum force measurement device 170, the flow rate measurement device 175, and the vitrector driver 180. The driver 155 interfaces with the intraocular light 110. The vitrector 105 interfaces with the infusion pump 160, the vacuum generator 165, the vacuum force measurement device 170, the flow rate measurement device 175, and the vitrector driver 180.

The surgical console 100 is typically a free-standing device with various user controls such as knobs and buttons, a display, such as an LCD display, and connection ports for various surgical instruments. The surgical console provides power to and controls the operation of the attached surgical instruments. In FIG. 1, a vitrector 105 and an intraocular light 105 are attached to the surgical console 100.

Vitrector 105 is designed to cut and remove the vitreous of an eye. Vitrector 105 has a cutter blade (not shown) that cuts the vitreous. In the embodiment depicted in FIG. 1, vitrector 105 also has an infusion line and an aspiration line. The infusion line provides irrigating solution to assist in a vitrectomy, and the aspiration line provides a vacuum force to remove the irrigating solution and the cut vitreous. Alternatively, lines separate from the vitrector may be used to provide infusion and aspiration.

Intraocular light 110 includes a light source which illuminates the inside of the eye through a small gauge fiber optic filament. In addition, in the embodiment of FIG. 1, intraocular light 110 includes a microscope designed to provide an image of the inside of the eye. In other embodiments, the microscope is separate from intraocular light 110. In either case, the surgeon uses the image of the inside of the eye to assist in manipulating the vitrector 105 to surgically remove the vitreous. Intraocular light 110 may also provide an indication of the media type. If the surgeon has the vitrector 105 correctly placed in the vitreous, then a green flash of light may be generated by intraocular light 110. If the surgeon has the vitrector 105 incorrectly placed in sterile irrigating solution, then a blue flash of light may be generated by intraocular light 110. In this manner, the surgeon is provided with a visual indication of the placement of vitrector 105.

While the indication of media type is depicted as a flash of intraocular light in FIG. 1, any other type of visual or audible indication may be used. For example, other types of visual indication include data displayed on the microscope display, data displayed on a screen on the console 100, or the illumination of a light emitting diode on console 100. Audible indications may include tones or electronic speech. In other embodiments of the present invention, the user is able to configure the method of indication. For example, different types of visual and audible indications may be offered. A user may be able to choose the indication type or types desired. In addition, the user may select that no indication be provided.

Controller 150 controls the operation of the various components in console 100 as well as the various instruments, such as vitrector 105 and intraocular light 110, attached to console 100. Controller 150 is typically an integrated circuit capable of performing logic functions. Controller 150 is typically in the form of a standard integrated circuit package with power, input, and output pins. In various embodiments, controller 150 is a targeted device controller. In such a case, controller 150 performs specific control functions targeted to a specific device or component, such as an infusion flow pump, a vacuum generator, or a cutter driver. For example, an infusion flow pump controller has the basic functionality to control an infusion flow pump. In other embodiments, controller 150 is a microprocessor. In such a case, controller 150 is programmable so that it can function to control an infusion pump as well as other components of the machine. Software loaded into the microprocessor implements the control functions provided by controller 150. In other cases, controller 150 is not a programmable microprocessor, but instead is a special purpose controller configured to control different components that perform different functions. While depicted as one component in FIG. 1, controller 150 may be made of many different components or integrated circuits.

Driver 155 is configured to drive intraocular light 110. In the embodiment shown, driver 155 provides a light source that is projected through a fiber optic filament in intraocular light 110 and into the eye. In addition, driver 155 receives an image of the inside of the eye for display. Driver 155 can include any commonly known device that generates light, such as a laser, light emitting diode, or lamp, and associated electronics to operate the light.

Infusion pump 160 is a pump designed to provide irrigating solution, such as a sterile saline solution, to the surgery site. Infusion pump 160 interfaces with an infusion line through which the fluid flows. In the embodiment of FIG. 1, infusion pump 160 provides irrigating solution to the inside of the eye during a vitrectomy. The fluid provided by infusion pump 160 helps to maintain the shape of the eye during surgery. Other liquids, like perfluorocarbon liquid and silicone oil, are typically injected into the eye with a syringe and are not pumped into the eye like irrigating solution. Infusion pump 160 can be any type of pump, such as a peristaltic pump, that pumps liquid.

Vacuum generator 165 provides an aspiration vacuum force to remove media from the eye during a vitrectomy. Vacuum generator 165 interfaces with an aspiration line that carries media from the eye and to a reservoir for disposal. Vacuum generator 165 typically employs a venturi effect to generate a vacuum force. Other commonly known methods of generating a vacuum force may also be employed.

Vacuum measurement device 170 measures the vacuum force provided by vacuum generator 165. Vacuum measurement device is located near the vacuum generator 165. Any commonly known measurement device may be employed to implement vacuum measurement device 170.

Flow rate measurement device 175 measures the fluid flow rate in the aspiration line. Flow rate measurement device 175 is located in series with or along the aspiration line between the vacuum generator 165 and the vitrector 105. Any commonly known measurement device may be employed to implement flow rate measurement device 175. Flow rate measurement device 175 may also be configured to measure the flow rate generated by the infusion portion of the machine. In such a case, flow rate measurement device 175 may be implemented with two separate flow rate measurement devices appropriately located in the console 100.

Vitrector driver 180 drives the cutting operation of the vitrector 105. Vitrector driver 180 may provide power to operate the vitrector 105 over a range of cut rates. For example, the vitrector 105 may be operated at a relatively slow cut rate of 400 cuts per minute or at a relatively high cut rate of 4000 cuts per minute. Vitrector driver 180 provides the necessary power to control the cut rate of vitrector 105.

In other embodiments of the present invention, controller 150 operates to record the time the vitrector 105 is located in a certain media type or in different media types. Alternatively, a separate device (not shown) that contains memory may be employed to record the time the vitrector 105 is located in a certain media type or in different media types. This recording function can assist in teaching a surgeon the proper placement of an instrument. Such a function can also be used for evaluative purposes.

In addition, the controller 150 may determine the configuration of the attached vitrector 105. For example, vitrector 105 may be a 25 gauge instrument. The size of vitrector 105 influences the vacuum force needed to achieve a certain aspiration flow rate. Controller 150 may also determine the operation or cut rate of the vitrector 105. The operation or cut rate of the vitrector 105 also influences the vacuum force needed to achieve a certain aspiration flow rate.

While shown as separate elements in console 100, the driver 155, the infusion pump 160, the vacuum generator 165, the vacuum force measurement device 170, the flow rate measurement device 175, and the vitrector driver 180 may be integrated into or divided into any number of components. The depiction of the blocks in FIG. 1 is purely for illustrative purposes and is not intended to limit the configuration of the components actually contained within console 100. For example, the microscope and light functions of driver 155 may be separated into and provided by different functional components. Likewise, the vacuum measurement device 170 and flow rate measurement device 175 may be integrated into a single set of components, some of which may perform functions for both measurements.

Figure 2:
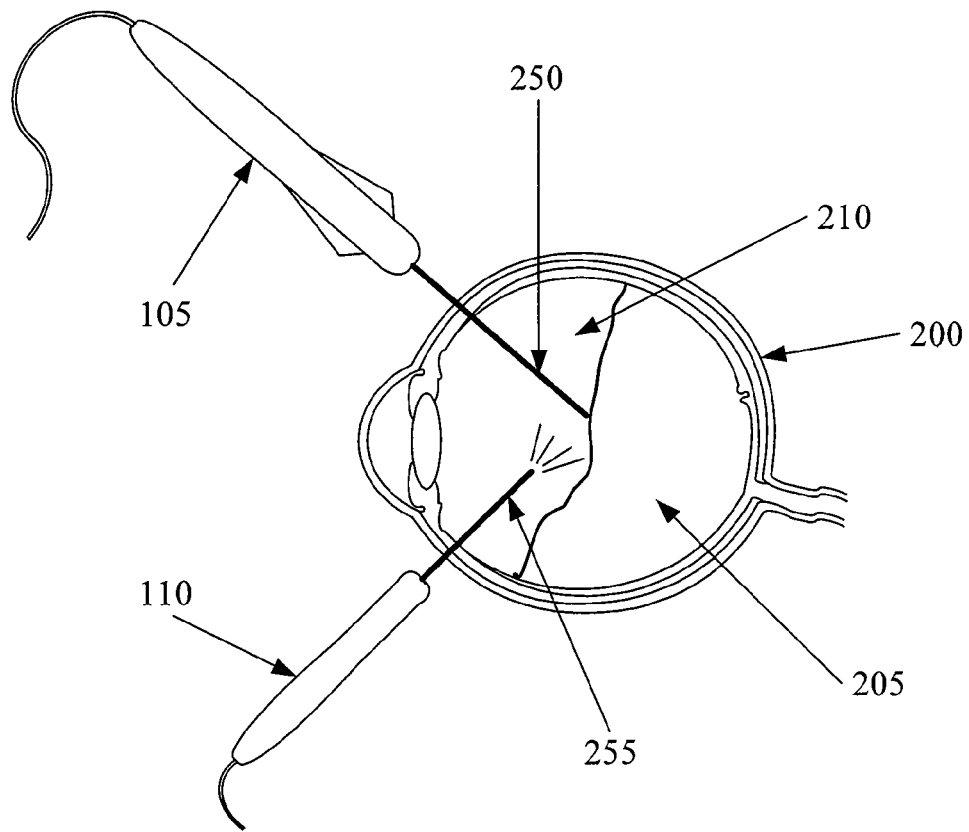
FIG. 2 is an operating view of an ophthalmic surgical system for identifying intraocular media types according to an embodiment of the present invention.

FIG. 2 is an operating view of an ophthalmic surgical system for identifying intraocular media types according to an embodiment of the present invention. In FIG. 2, eye 200 has two volumes—the volume in which vitreous is present 205 and the volume in which vitreous is absent or has been removed 210. The line dividing these two volumes is the interface between them. Vitrector probe 250 of vitrector 105 is inserted into the eye 200 through its pars plana region. Likewise, light probe 255 of intraocular light 110 is inserted into the eye 200 through its pars plana region.

In the configuration depicted in FIG. 2, a vitrectomy is in the process of being performed. The vitrector 105 has removed the vitreous from volume 210, and is removing the vitreous at the interface of volumes 205 and 210. The vitrector probe 250 cuts the vitreous and aspirates a mixture of cut vitreous and irrigating solution from the eye. Irrigating solution is being provided through an infusion line in the vitrector probe 250 and a vacuum force is being provided through an aspiration line in vitrector probe 250.

In FIG. 2, intraocular light 110 is illuminated. Light probe 255 illuminates the interior of the eye 200 so that the surgeon can manipulate the vitrector 105 to cut and remove the vitreous 205. Intraocular light 110 may also provide an indication of the media type as previously discussed.

Figure 3:
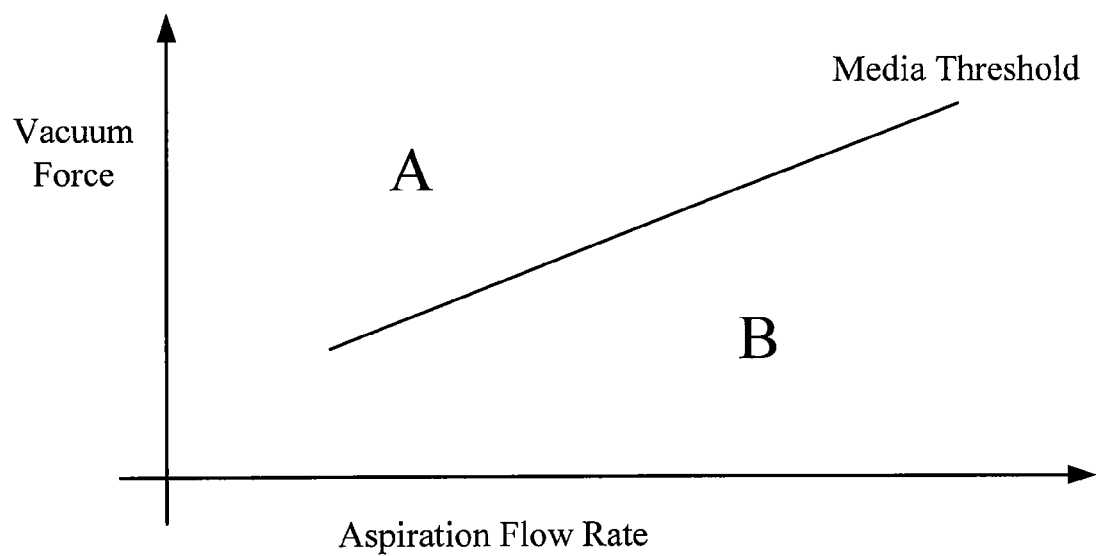
FIG. 3 is an exemplary graph of a media threshold according to an embodiment of the present invention.
Figure 4:
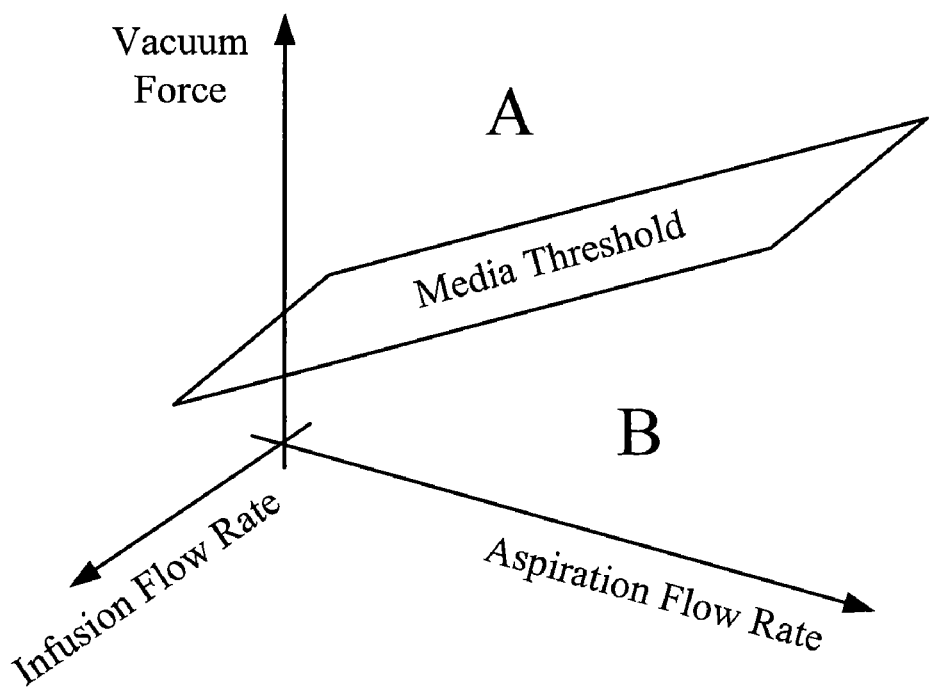
FIG. 4 is an exemplary graph of a media threshold according to an embodiment of the present invention.
Figure 5:
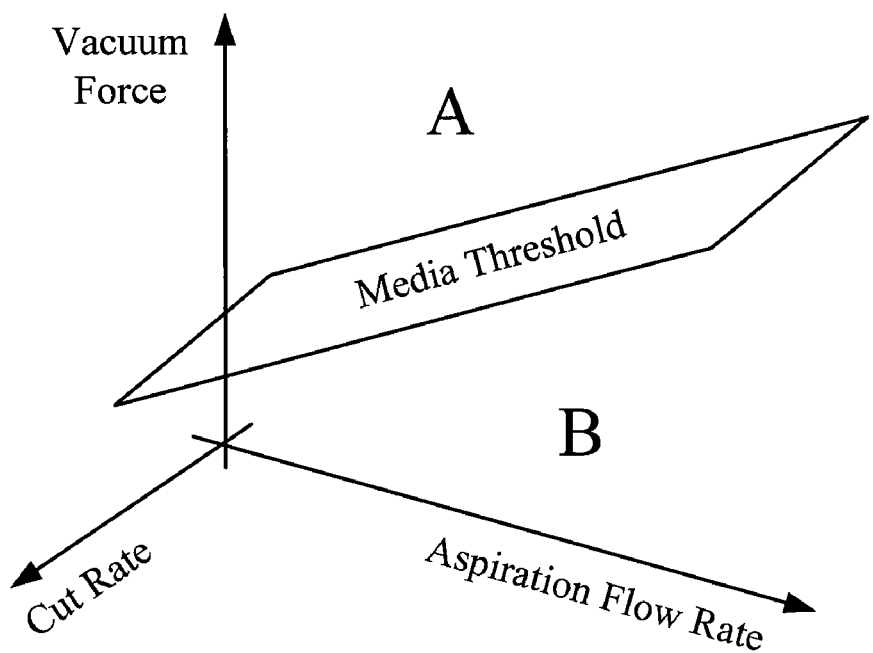
FIG. 5 is an exemplary graph of a media threshold according to an embodiment of the present invention.

FIGS. 3, 4 and 5 are exemplary graphs of media thresholds according to various embodiments of the present invention. In each of these Figures, a media threshold is depicted. The media threshold is a line (in FIG. 3) or a surface (in FIGS. 4 and 5) that divides the graph area into two regions. One region (region A) lies above the line or surface, and the other region (region B) lies below the line or surface. One media has properties, that when plotted on the graph, lie in region A, and another media has properties, that when plotted on the graph, lie in region B. As previously mentioned, different media have different properties that can be characterized by an aspiration flow rate produced by a vacuum force for a given instrument configuration and operation. In this manner, the variables depicted on the various graphs include: the vacuum force, the aspiration flow rate, the infusion flow rate, and the instrument operation (in the case of a vitrector, the cut rate).

FIG. 3 depicts a media threshold based on two plotted variables—the vacuum force produced in the instrument and the aspiration flow rate produced by that vacuum force. In FIG. 3, a set of graphs for a given surgical instrument over a range of infusion flow rates can be used to determine the media type into which the vitrector is inserted. For a given instrument configuration and operation and a given infusion flow rate, the type of media can be determined from the vacuum force required to achieve a given aspiration flow rate. In other words, in ophthalmic surgery, a 25 gauge vitrector operating a given cut rate with a given infusion flow rate can produce a range of different vacuum forces. This range of different vacuum forces results in different aspiration flow rates depending on the media type being aspirated. In general, a higher vacuum force results in a higher aspiration flow rate. However, the aspiration flow rate depends on the media being aspirated. Media with higher viscosities require higher vacuum forces to produce a given aspiration flow rate. Likewise, media with lower viscosities require lower vacuum forces to produce the same aspiration flow rate. In this manner, the aspiration flow rate is related to the viscosity of the media being aspirated.

For example, intraocular irrigating solution has a viscosity of about one centistoke at room temperature. Perfluorocarbon liquid has a viscosity of about 0.7 centistokes, and silicone oil has a viscosity of about 1000 centistokes. The vitreous in a human eye generally has a viscosity over a range of about two to six centistokes. The human vitreous becomes less viscous over time as a part of the aging process.

In the graph of FIG. 3, in region A, a higher flow rate is obtained for a given probe operation and vacuum force. In region B, a lower flow rate is obtained for a given probe operation and vacuum force. Data points for lower viscosity media, such as BSS or perfluorocarbon fluid, reside in region A. Data points for higher viscosity media, such as vitreous or a mixture of vitreous and BSS, reside in region B. Intuitively, it takes more vacuum force to create a given flow rate for a higher viscosity material than it does for a lower viscosity material.

The controller 150 of FIG. 1 utilizes information about the vacuum force, the aspiration flow rate, the infusion flow rate, and the instrument operation (in the case of a vitrector, the cut rate) to determine the media type. While FIG. 3 is depicted as a graph for illustrative purposes, controller 150 may utilize a table of numbers as well. The table of numbers can correspond to the media threshold line plotted on the graph.

FIG. 4 depicts a media threshold based on three plotted variables—the vacuum force produced in the instrument, the aspiration flow rate produced by that vacuum force, and the infusion flow rate. In FIG. 4, a set of graphs for a given surgical instrument over an operating range of that instrument can be used to determine the media type into which the vitrector is inserted. The graph of FIG. 4 simply adds an extra plotted variable to the graph of FIG. 3. FIG. 4 provides a visual representation of a media threshold surface for illustrative purposes. In FIG. 4, data points for lower viscosity media, such as BSS or perfluorocarbon fluid, reside in region A. Data points for higher viscosity media, such as vitreous or a mixture of vitreous and BSS, reside in region B.

Likewise, FIG. 5 depicts a media threshold based on three plotted variables—the vacuum force produced in the instrument, the aspiration flow rate produced by that vacuum force, and the operation of the surgical instrument (in this case, the cut rate of the vitrector). In FIG. 5, a set of graphs for a given surgical instrument over a range of infusion flow rates can be used to determine the media type into which the vitrector is inserted. The graph of FIG. 5 simply adds an extra plotted variable to the graph of FIG. 3. FIG. 5 provides a visual representation of a media threshold surface for illustrative purposes. In FIG. 5, data points for lower viscosity media, such as BSS or perfluorocarbon fluid, reside in region A. Data points for higher viscosity media, such as vitreous or a mixture of vitreous and BSS, reside in region B.

While depicted as graphs, FIGS. 3, 4, and 5 can be represented as a table or set of values. Measured values greater than those contained in the set represent media in region A. Measured values less than those contained in the set represent media in region B. A distance or direction may be calculated between values in the set and the measured values. A positive distance or direction can indicate media in region A. Likewise, a negative distance or direction can indicate media in region B. Any number of known mathematical methods may be used to determine the location of the measured data points on a given graph.

Figure 6:
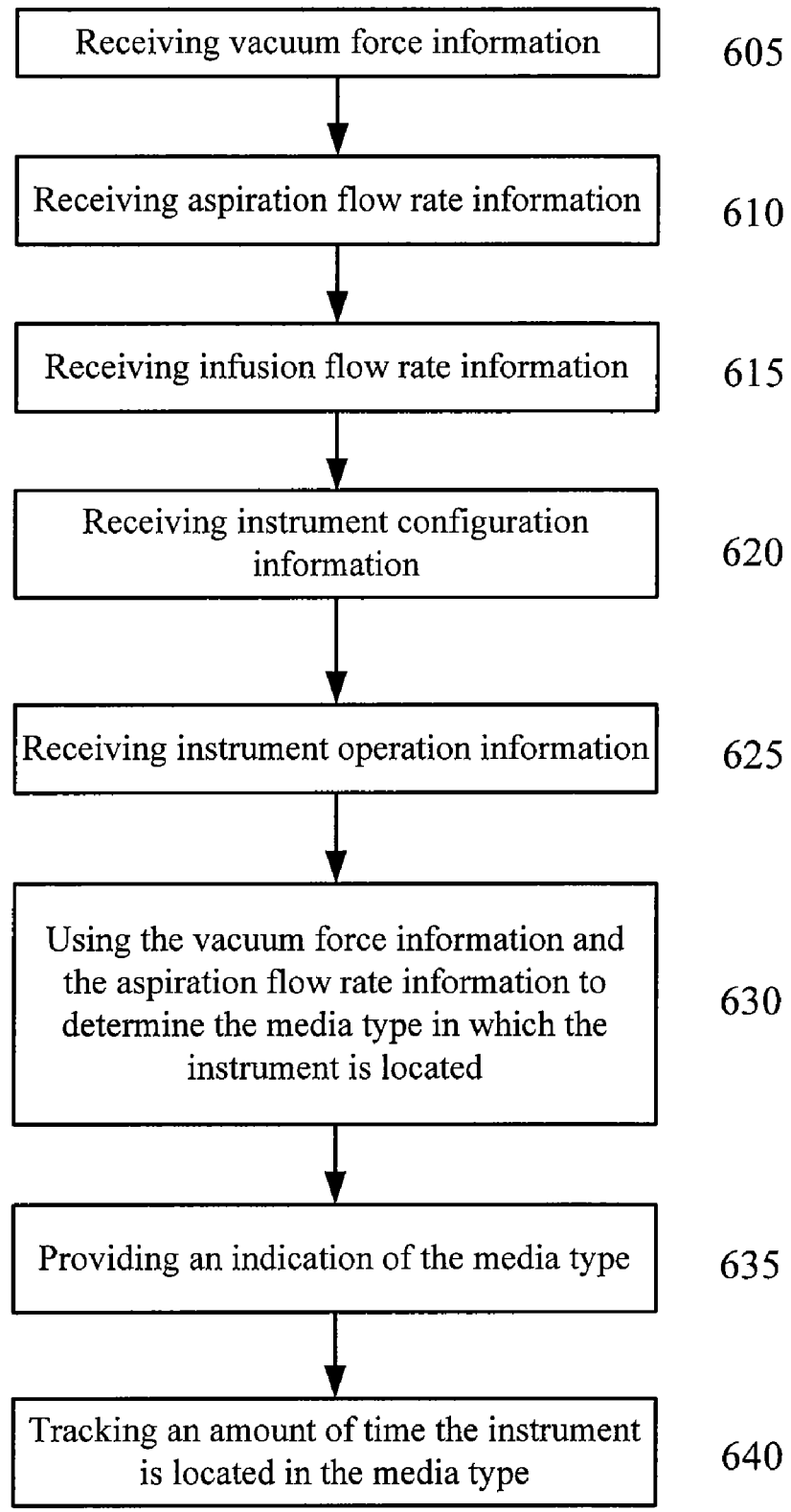
FIG. 6 is a flow chart depicting one method of operation of the present invention.

FIG. 6 is a flow chart depicting one method of operation of the present invention. In 605, vacuum force information is received. In 610, aspiration flow rate information is received. In 615, infusion flow rate information is received. In 620 instrument configuration information is received. In 625, instrument operation information is received. In 630, the vacuum force and flow rate information is used to determine the media type in which the instrument is located. In 635, an indication of the media type is provided. In 640, an amount of time the instrument is located in the media type is tracked.

From the above, it may be appreciated that the present invention provides an improved system and methods for providing an indication of media types during surgery. The present invention provides a user selectable identification method. The invention determines the media type into which a vitrector is inserted based on a vacuum force, aspiration flow rate and other variables. The invention characterizes the media type based on the amount of vacuum force required to produce a given aspiration flow rate for a given instrument configuration and operation. The present invention is illustrated herein by example, and various modifications may be made by a person of ordinary skill in the art.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A surgical system comprising:
   a surgical instrument that can be located in a media type, the surgical instrument having an aspiration portion;
   an aspiration flow rate measurement device configured to measure a flow rate generated by the aspiration portion;
   a vacuum force measurement device configured to measure a vacuum force generated by the aspiration portion; and
   an indicator configured to provide an indication of the media type in which the surgical instrument is located;
   wherein the system is configured to distinguish between at least three different media types based on the measured aspiration flow rate and the measured vacuum force.

2. The system of claim 1 further comprising:
   a device for identifying a configuration and operation of the surgical instrument.

3. The system of claim 1 wherein the surgical instrument is a vitrector.

4. The system of claim 3 wherein the indicator is an intraocular light.

5. The system of claim 1 in which the indication of the media type is visually displayed.

6. The system of claim 1 in which the indication of the media type is audibly displayed.

7. The system of claim 1 in which the indication of the media type is user-assigned.

8. The system of claim 1 in which the indicator is capable of being selectively turned on or off.

9. The system of claim 1, wherein the at least three different media types include vitreous, perfluorocarbon liquid, silicone oil, and sterile intraocular irrigating solution.

10. The system of claim 1, wherein the system is further configured to use an operation and configuration of the surgical instrument in distinguishing between the at least three different media types.

11. The system of claim 1 further comprising:
a device for tracking an amount of time the surgical instrument is located in the media type.

12. The system of claim 1 in which the surgical instrument further comprises an infusion portion and the system further comprises a device for measuring a flow rate generated by the infusion portion;
wherein the system is further configured to use the measured infusion portion flow rate in distinguishing between the at least three different media types.

13. A method for identifying a media type in which a surgical instrument is located comprising:
measuring vacuum force;
measuring aspiration flow rate;
using the measured vacuum force and the measured aspiration flow rate to distinguish between at least three different media types the instrument is located; and
providing an indication of the media type.

14. The method of claim 13 in which providing an indication of the media type comprises providing an intraocular light.

15. The method of claim 13 in which providing an indication of the media type comprises visually displaying the indication.

16. The method of claim 13 in which providing an indication of the media type comprises audibly displaying the indication.

17. The method of claim 13 wherein providing an indication of the media type further comprises:
receiving a user-assigned identification type.

18. The method of claim 13 further comprising:
tracking an amount of time the surgical instrument is located in the media type.

19. The method of claim 13 further comprising:
measuring infusion flow rate;
wherein the method further comprises using the measured infusion flow rate to distinguish between the at least three different media types.

20. The method of claim 13 further comprising:
receiving information about a configuration and operation of the surgical instrument.

21. The method of claim 13, wherein the at least three different media types include vitreous, perfluorocarbon liquid, silicone oil, and sterile intraocular irrigating solution.

* * * * *